US008653123B2

(12) United States Patent
Dibas et al.

(10) Patent No.: US 8,653,123 B2
(45) Date of Patent: *Feb. 18, 2014

(54) ESTER PRO-DRUGS OF [3-(1-(1H-IMIDAZOL-4-YL)ETHYL)-2-METHYLPHENYL] METHANOL FOR TREATING RETINAL DISEASES

(75) Inventors: Mohammad I. Dibas, Laguna Niguel, CA (US); Daniel W. Gil, Corona Del Mar, CA (US); Ken Chow, Newport Coast, CA (US); Liming Wang, Irvine, CA (US); Michael E. Garst, Newport Beach, CA (US); John E. Donello, Dana Point, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/233,382

(22) Filed: Sep. 15, 2011

(65) Prior Publication Data

US 2012/0149746 A1    Jun. 14, 2012

Related U.S. Application Data

(60) Provisional application No. 61/383,370, filed on Sep. 16, 2010.

(51) Int. Cl.
*A61K 31/415* (2006.01)

(52) U.S. Cl.
USPC .......................... 514/396; 514/385; 514/913

(58) Field of Classification Search
USPC .......................... 514/385, 396, 913
See application file for complete search history.

(56) References Cited

U.S. PATENT DOCUMENTS

| 5,459,133 A * | 10/1995 | Neufeld .................. 514/215 |
| 2004/0214829 A1 * | 10/2004 | Graham et al. ............. 514/249 |
| 2011/0301214 A1 * | 12/2011 | Gil .................... 514/400 |

FOREIGN PATENT DOCUMENTS

| WO | 9514007 | 5/1995 |
| WO | 2005034998 | 4/2005 |
| WO | 2006036480 | 4/2006 |
| WO | 2009089132 | 7/2009 |
| WO | 2010091209 | 8/2010 |
| WO | WO 2010093930 | 8/2010 |

OTHER PUBLICATIONS

Newman, Hereditary Optic Neuropathies: From the Mitochondria to the Optic Nerve, Sep. 2005, American Journal of Ophthalmology, 140, 517-523.*
Moss, Leber's Congenital Amaurosis, http://www.tsbvi.edu/Outreach/seehear/spring01/lebers.htm, printed Apr. 27, 2008, 3 pages.*
Merck Manual, Central Retinal Vein Occlusion, 2005, http://www.merck.com/mmpe/print/sec09/ch106/ch106d.html, printed Jun. 5, 2008, 1 page.*
Mayo Clinic, Stargardt's disease: Can it be treated?, 2006, printed May 27, 2008, MayoClinic.com, http://www.mayoclinic.com/print/stargardts-disease/AN00846/METHOD=print, 2 pages.*
MedlinePlus, Macular degeneration, U.S. National Library of Medicine and National Institutes of Health, Aug. 4, 2008, printed from http://www.nlm.nih.gov/medlineplus/print/ency/article/001000.htmon Jun. 11, 2009, 3 pages.*
Merck Manuals, Retinitis Pigmentosa, 2005, http://www.merck.com/mmpe/print/sec09/ch106/ch106h.html, printed May 27, 2008, 2 pages.*
Vippagunta et al., Crystalline solids, 2001, Advanced:Drug Delivery Reviews, 48, 3-26.*
Braga et al., Chem. Commun., "Making Crystals from Crystals: a green route to crystal engineering and polymorphism," 2005, pp. 3635-3645.*
Seddon, K.R., "Pseudopolymorph: a polemic," Crystal Growth & Design, 2004, 4(6), pp. 1087, web release date Oct. 19, 2004.*
Hui, Y.-H et al.; "Analytical method development for the simultaneous quantitation of dexmedetomidine and three potential metabolites in plasma"; Journal of Chromatography, (1997), 762(1+2), 281-291.
Stoilov et al.; "Synthesis of detomidine and medetomidine metabolites: 1,2,3-trisubstituted arenes with 4'(5')-imidazolylmethyl groups" in Journal of Heterocyclic Chemistry (1993), 30(6), (1645-1651).
Salonen, et al. "Biotransformation of Medetomidine in the Rat" in Xenobiotica (1990), 20(5), 471-80.
Pierce V. Kavanagh; "Synthesis of Possible Metabolites of Medetomidine {1-(2,3-Dimethylphenyl)-1-[imidazol-4(5)-yl] ethane}"; J. Chem. Research (S), 1993.
Larry Wheeler, From the Lab to the Clinic: Activation of an Alpha-2 Agonist Pathway is Neuroprotective in Models of Retinal and Optic Nerve Injury, Eur. J. Ophthalmology, 1999, 9 (1), S17-S22.
Bernard Testa, Design of Intramolecularly Activated Prodrugs, Drug Metabolism Reviews, 1998, 30 (4), 787-807.
Vincent Lee, Prodrugs for Improved Ocular Drug Delivery, Advanced Drug Delivery Reviews, 1989, 3 (1), 1-38.
Saul Merin, A Pilot Study of Topical Treatment with an a2-Agonist in Patients with Retinal Dystrophies, J. Ocular Pharmacology and Therapeutics, 2008, 24 (1), 80-86.
T. Higuchi and V. Stella, "Pro-drugs as Novel Delivery System", vol. 14 of the A.C.S. Symposium Series, Jun. 1, 1975, p. 9 and p. 66 to 73.
Edward B. Roche, "Bioreversible Carriers in Drug Design", American Pharmaceutical Association and Pergamon Press, 1987, Chapter 4, p. 121-163.

* cited by examiner

*Primary Examiner* — Gigi Huang
(74) *Attorney, Agent, or Firm* — Doina G. Ene

(57) ABSTRACT

The present invention relates to method of treating retinal diseases in a subject in need of such treatment, which comprises administering a therapeutically effective amount of a composition comprising a ester pro-drugs of [3-(1-(1H-imidazol-4-yl)ethyl) -2-methylphenyl]methanol, processes for preparing them, pharmaceutical compositions containing them and their use as pharmaceuticals.

7 Claims, No Drawings

ESTER PRO-DRUGS OF [3-(1-(1H-IMIDAZOL-4-YL)ETHYL)-2-METHYLPHENYL] METHANOL FOR TREATING RETINAL DISEASES

RELATED APPLICATIONS

This application claims priority to U.S. Provisional Patent Application No. 61/383,370 filed on Sep. 16, 2010, the entire disclosure of which is incorporated herein by this reference.

BACKGROUND OF THE INVENTION

1. Field of the Invention

The present invention relates to a method for treating retinal diseases in a subject in need of such treatment, which comprises administering a therapeutically effective amount of a composition comprising ester pro-drugs of [3-(1-(1H-imidazol-4-yl)ethyl)-2-methylphenyl]methanol or of its enantiomers.

2. Summary of the Related Art

Three alpha-1 and three alpha-2 adrenergic receptors have been characterized by molecular and pharmacological methods. Activation of these alpha receptors evokes physiological responses with useful therapeutic applications.

Compound, 4-[1-(2,3-dimethylphenyl)ethyl]-3H-imidazole, generically known as, medetomidine is an alpha 2 adrenergic agonist, for use in the sedation of animals. The hydrochloride salt of the (S) enantiomer of medetomidine, generically known as dexmedetomidine, (S) 4-[1-(2,3-dimethylphenyl)ethyl]-3H-imidazole, is also indicated for use as a sedative or analgesic in cats and dogs.

The metabolite of dexmedetomidine is (S) [3-(1-(1H-imidazol-4-yl)ethyl)-2-methylphenyl]methanol together with its racemic mixture, compound [3-(1-(1H-imidazol-4-yl)ethyl)-2-methylphenyl]methanol, are described in the literature in *Journal of Chromatography*, (1997), 762(1+2), 281-291 by Hui, Y.-H et al.

[3-(1-(1H-imidazol-4-yl)ethyl)-2-methylphenyl]methanol is described in "Synthesis of detomidine and medetomidine metabolites: 1,2,3-trisubstituted arenes with 4'(5')-imidazolylmethyl groups" in *Journal of Heterocyclic Chemistry* (1993), 30(6), (1645-1651) by Stoilov et al.

Kavanagh, et al. describe [3-(1-(1H-imidazol-4-yl)ethyl)-2-methylphenyl]methanol in "Synthesis of Possible Metabolites of Medetomidine {1-(2,3-dimethylphenyl)-1-[imidazol-4(5)-yl]ethane" in *Journal of Chemical Research, Synopses* (1993), (4), 152-3.

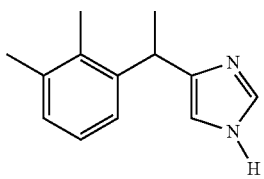

Medetomidine 4-(1-(2,3-dimethylphenyl)ethyl)-1H-imidazole

CAS 86347-14-0

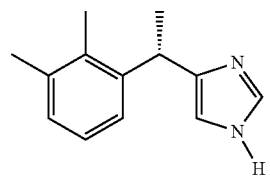

Dexmedetomidine (S)-4-(1-(2,3-dimethylphenyl)ethyl)-1H-imidazole

CAS 189255-79-6

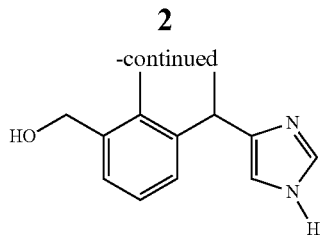

(3-(1-(1H-imidazol-4-yl)ethyl)-2-methylphenyl)methanol

CAS 128366-50-7

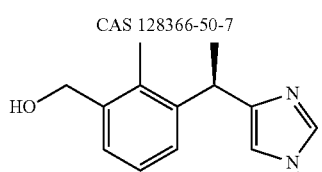

(R)-(3-(1-(1H-imidazol-4-yl)ethyl)-2-methylphenyl)methanol

CAS 1240244-32-9

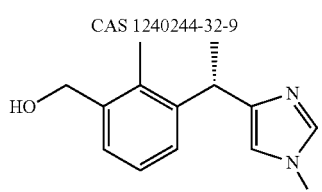

(S)-(3-(1-(1H-imidazol-4-yl)ethyl)-2-methylphenyl)methanol

CAS 189255-79-6

[3-(1-(1H-imidazol-4-yl)ethyl)-2-methylphenyl)methanol] is described by Salonen, et al. in "Biotransformation of Medetomidine in the Rat" in *Xenobiotica* (1990), 20(5), 471-80.

PCT Int. Appl. WO 2010093930 A1 discloses [3-(1-(1H-imidazol-4-yl)ethyl)-2-methylphenyl]methanol and its (S) and (R) enantiomers.

SUMMARY OF THE INVENTION

Three alpha 1 and three alpha 2 adrenergic receptors have been characterized by molecular and pharmacological methods. Activation of these alpha 2 receptors evokes physiological responses and has useful therapeutic actions.

The present invention relates to a method of treating retinal diseases in a subject in need of such treatment, which comprises administering a therapeutically effective amount of a composition comprising ester pro-drugs of [3-(1-(1H-imidazol-4-yl)ethyl)-2-methylphenyl]methanol. Upon hydrolytic and/or enzymatic cleavage of the ester functionality the parent compound, [3-(1-(1H-imidazol-4-yl)ethyl)-2-methylphenyl]methanol, is released to act as a selective modulator of the alpha 2 adrenergic receptors.

In another aspect, the present invention relates to a method treating retinal diseases in a subject in need of such treatment, which comprises administering a therapeutically effective amount of a composition comprising ester pro-drugs of (S) [3-(1-(1H-imidazol-4-yl)ethyl)-2-methylphenyl]methanol, or pharmaceutical compositions containing them. Upon hydrolytic and/or enzymatic cleavage of the ester functionality the parent compound, active metabolite, (S) [3-(1-(1H-imidazol-4-yl)ethyl)-2-methylphenyl]methanol, is released to act as a selective modulator of the alpha 2 adrenergic receptors.

In another aspect the present invention provides relates to a method treating retinal diseases in a subject in need of such treatment, which comprises administering a therapeutically effective amount of a composition comprising ester pro-drugs of (R) [3-(1-(1H-imidazol-4-yl)ethyl)-2-methylphenyl]methanol, or pharmaceutical compositions containing them. Upon hydrolytic and/or enzymatic cleavage of the ester functionality the parent compound (R) [3-(1-(1H-imidazol-4-yl)ethyl)-2-methylphenyl]methanol, is released to act as a selective modulator of the alpha 2 adrenergic receptors.

The ester pro-drugs of [3-(1-(1H-imidazol-4-yl)ethyl)-2-methylphenyl]methanol are useful for the treatment or prevention of mammals, including humans, in a range of conditions and diseases that are alleviated by alpha 2A, 2B, 2C activation, including but not limited to treating or preventing glaucoma, elevated intraocular pressure, ischemic neuropathies, optic neuropathy, pain, visceral pain, corneal pain, headache pain, migraine, cancer pain, back pain, irritable bowl syndrome pain, muscle pain and pain associated with diabetic neuropathy, the treatment of diabetic retinopathy, other retinal degenerative conditions, stroke, cognitive deficits, neuropsychiatric conditions, drug dependence and addiction, withdrawal of symptoms, obsessive-compulsive disorders, obesity, insulin resistance, stress-related conditions, diarrhea, diuresis, nasal congestion, spasticity, attention deficit disorder, psychoses, anxiety, depression, autoimmune disease, Crohn's disease, gastritis, Alzheimer's, and Parkinson's ALS other neurodegenerative diseases, dermatological conditions, skin erythema (redness) and inflammation, acne, age related macular degeneration, wet macular degeneration, dry macular degeneration, geographic atrophy, diabetic macular edema, tumors, wound healing, inflammation and retinal vein occlusion, enhancing vision in patients with vision loss from conditions including glaucoma, retinitis pigmentosa and neuritis secondary to multiple sclerosis, rosacea (dilation of the blood vessels just under the skin), sunburn, chronic sun damage, discreet erythemas, psoriasis, acne rosacea, menopause-associated hot flashes, hot flashes resulting from orchiectomyatopic dermatitis, photoaging, seborrheic dermatitis, allergic dermatitis, redness of the skin, telangiectasia (dilations of previously existing small blood vessels) of the face, rhinophymia (hypertrophy of the nose with follicular dilation), red bulbous nose, acne-like skin eruptions (may ooze or crust), burning or stinging sensation of the face, irritated and bloodshot and watery eyes, erythema of the skin, cutaneous hyperactivity with dilation of blood vessels of the skin, Lyell's syndrome, Stevens-Johnson syndrome, erythema multiforme minor, erythema multiforme major and other inflammatory skin diseases.

DETAILED DESCRIPTION OF THE INVENTION

The present invention relates to a method of treating retinal diseases in a subject in need of such treatment, which comprises administering a therapeutically effective amount of a composition comprising ester pro-drugs of [3-(1-(1H-imidazol-4-yl)ethyl)-2-methylphenyl]methanol of (S) [3-(1-(1H-imidazol-4-yl)ethyl)-2-methylphenyl]methanol and of (R) [3-(1-(1H-imidazol-4-yl)ethyl)-2-methylphenyl]methanol as alpha-2 agonists with therapeutic utility.

The term "subject", as used herein, refers to a human patient.

In a preferred embodiment the present invention relates to a method of treating retinal diseases in a subject in need of such treatment, which comprises administering a therapeutically effective amount of a composition comprising esters pro-drugs of (S)-[3-(1-(1H-imidazol-4-yl)ethyl)-2-methylphenyl]methanol as alpha-2 agonists with therapeutic utility. Upon hydrolytic or enzymatic cleavage of the ester functionality the parent compound, active metabolite, (S)-[3-(1-(1H-imidazol-4-yl)ethyl)-2-methylphenyl]methanol, is released to act as a selective modulator of the alpha 2 adrenergic receptors.

In one aspect of the invention, there is provided a method for treating retinal diseases in a patient in need thereof which comprises, consists essentially of or consists of or consists of administering a therapeutically effective amount of a pharmaceutical composition comprising, consisting essentially of or consisting of a therapeutically effective amount of ester pro-drugs of [3-(1-(1H-imidazol-4-yl)ethyl)-2-methylphenyl]methanol, or the tautomers thereof, or pharmaceutically acceptable salts thereof.

In another aspect of the invention, there is provided a method for treating retinal diseases in a patient in need thereof which comprises, consists essentially of or consists of or consists of administering a therapeutically effective amount of a pharmaceutical composition comprising, consisting essentially of or consisting of a therapeutically effective amount of ester pro-drugs (S) [3-(1-(1H-imidazol-4-yl)ethyl)-2-methylphenyl]methanol, or the tautomers thereof, or pharmaceutically acceptable salts thereof.

In another aspect of the invention, there is provided a method for treating retinal diseases in a patient in need thereof which comprises, consists essentially of or consists of or consists of administering a therapeutically effective amount of a pharmaceutical composition comprising, consisting essentially of or consisting of a therapeutically effective amount of ester pro-drugs of (R) [3-(1-(1H-imidazol-4-yl)ethyl)-2-methylphenyl]methanol, or the tautomers thereof, or pharmaceutically acceptable salts thereof.

In another aspect of the invention, there is provided a method for treating retinal diseases including but not limited to: age related macular degeneration, wet macular degeneration, dry macular degeneration, geographic atrophy, diabetic retinopathy, diabetic macular edema and retinal vein occlusion. Our compound of interest is also useful for enhancing vision in patients with vision loss from conditions including ocular hypertension, glaucoma, retinitis pigmentosa, nyctalopia, and neuritis secondary to multiple sclerosis.

In another aspect of the invention, there is provided a method for treating retinal diseases including but not limited to: age related macular degeneration, wet macular degeneration, dry macular degeneration, geographic atrophy, diabetic retinopathy, diabetic macular edema and retinal vein occlusion. Our compound of interest is also useful for enhancing vision in patients with vision loss from conditions including ocular hypertension, glaucoma, retinitis pigmentosa, nyctalopia, and neuritis secondary to multiple sclerosis, which comprises, consists essentially of or consists of or consists of administering a therapeutically effective amount of a pharmaceutical composition comprising, consisting essentially of or consisting of a therapeutically effective amount of ester pro-drugs of [3-(1-(1H-imidazol-4-yl)ethyl)-2-methylphenyl]methanol, or the tautomers thereof, or pharmaceutically acceptable salts thereof.

In another aspect of the invention, there is provided a method for treating retinal diseases including but not limited to: including but not limited to age related macular degeneration, wet macular degeneration, dry macular degeneration, geographic atrophy, diabetic retinopathy, diabetic macular edema and retinal vein occlusion. Our compound of interest is also useful for enhancing vision in patients with vision loss from conditions including ocular hypertension, glaucoma, retinitis pigmentosa, nyctalopia, and neuritis secondary to multiple sclerosis, which comprises, consists essentially of or consists of or consists of administering a therapeutically effective amount of a pharmaceutical composition comprising, consisting essentially of or consisting of a therapeutically effective amount of ester pro-drugs of (S) [3-(1-(1H-imidazol-4-yl)ethyl)-2-methylphenyl]methanol, or the tautomers thereof, or pharmaceutically acceptable salts thereof.

In another aspect of the invention, there is provided a method for treating retinal diseases including but not limited to: including but not limited to age related macular degeneration, wet macular degeneration, dry macular degeneration, geographic atrophy, diabetic retinopathy, diabetic macular edema and retinal vein occlusion. Our compound of interest is also useful for enhancing vision in patients with vision loss from conditions including ocular hypertension, glaucoma, retinitis pigmentosa, nyctalopia, and neuritis secondary to multiple sclerosis, which comprises, consists essentially of or consists of or consists of administering a therapeutically effective amount of a pharmaceutical composition comprising, consisting essentially of or consisting of a therapeutically effective amount of ester pro-drugs of (R) [3-(1-(1H-imidazol-4-yl)ethyl)-2-methylphenyl]methanol, or the tautomers thereof, or pharmaceutically acceptable salts thereof.

In another aspect of the invention, there is provided a method for treating retinal diseases wherein the pharmaceutical composition comprising, consisting essentially of or consisting of a therapeutically effective amount ester pro-drugs of [3-(1-(1H-imidazol-4-yl)ethyl)-2-methylphenyl]methanol, is selected from topical ocular application, direct injection, applications and formulations that may further enhance the long duration of actions such as a slow releasing pellet, suspension, gel, solution, cream, ointment, foams, emulsions, microemulsions, serums, aerosols, sprays, dispersions, microcapsules, vesicles, microparticles.

In another aspect of the invention, there is provided a method for treating retinal diseases wherein the pharmaceutical composition comprising, consisting essentially of or consisting of a therapeutically effective amount of ester pro-drugs of (S) [3-(1-(1H-imidazol-4-yl)ethyl)-2-methylphenyl]methanol is selected from topical ocular application, direct injection, applications and formulations that may further enhance the long duration of actions such as a slow releasing pellet, suspension, gel, solution, cream, ointment, foams, emulsions, microemulsions, serums, aerosols, sprays, dispersions, microcapsules, vesicles, microparticles.

In another aspect of the invention, there is provided a method for treating retinal diseases wherein the pharmaceutical composition comprising, consisting essentially of or consisting of a therapeutically effective amount of ester pro-drugs of (R) [3-(1-(1H-imidazol-4-yl)ethyl)-2-methylphenyl]methanol is selected from topical skin application, direct injection, applications and formulations that may further enhance the long duration of actions such as a slow releasing pellet, suspension, gel, solution, lotion, cream, ointment, foams, emulsions, microemulsions, serums, aerosols, sprays, dispersions, microcapsules, vesicles, microparticles.

"Prodrugs" are frequently referred to by the term "metabolically cleavable derivatives" which refers to compound forms which are rapidly transformed in vivo to the parent compound according to the invention, for example, by hydrolysis in blood. Thus, prodrugs are compounds bearing groups which are removed by biotransformation prior to exhibiting their pharmacological action. Such groups include moieties which are readily cleaved in vivo from the compound bearing it, which compound after cleavage remains or becomes pharmacologically active. Such metabolically cleavable groups form a class well known to practitioners of the art. They include, but are not limited to such groups as alkanoyl (i.e. acetyl, propionyl, butyryl, and the like), unsubstituted and substituted carbocyclic aroyl (such as benzoyl, substituted benzoyl and 1- and 2-naphthoyl), alkoxycarbonyl (such as ethoxycarbonyl), trialklysilyl (such as trimethyl- and triethylsilyl), monoesters formed with dicarboxylic acids (such as succinyl), phosphate, sulfate, sulfonate, sulfonyl, sulfinyl and the like. The compounds bearing the metabolically cleavable groups have the advantage that they may exhibit improved bioavailability as a result of enhanced solubility and/or rate of absorption conferred upon the parent compound by virtue of the presence of the metabolically cleavable group. (T. Higuchi and V. Stella, "Pro-drugs as Novel Delivery System", Vol. 14 of the A.C.S. Symposium Series; "Bioreversible Carriers in Drug Design", ed. Edward B. Roche, American Pharmaceutical Association and Pergamon Press, 1987).

In one aspect, the invention therefore relates to a method of lowering intraocular pressure in a subject in need of such treatment, which comprises administering a therapeutically effective amount of a composition comprising a compound having Formula I, its individual enantiomers, its individual diastereoisomers, its individual hydrates, its individual solvates, its individual crystal forms, its individual isomers, its individual tautomers or a pharmaceutically acceptable salt thereof,

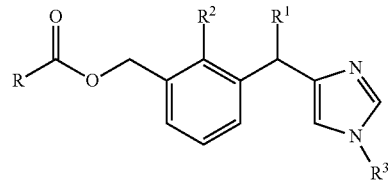

Formula I wherein
$R^1$ is H or $C_{1-3}$ alkyl;
$R^2$ is H or $C_{1-3}$ alkyl;
$R^3$ is H, $C_{1-10}$ alkyl, heterocycle or aryl; and
R is $C_{1-10}$ alkyl, heterocycle or aryl.

In a preferred aspect, the invention therefore relates to a method of lowering intraocular pressure in a subject in need of such treatment, which comprises administering a therapeutically effective amount of a composition comprising a compound having Formula II, its individual diastereoisomers, its individual hydrates, its individual solvates, its individual crystal forms, its individual isomers, its individual tautomers or a pharmaceutically acceptable salt thereof,

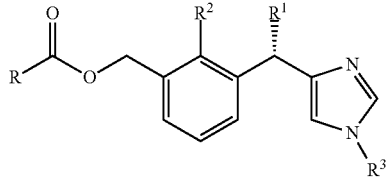

Formula II wherein
$R^1$ is H or $C_{1-3}$ alkyl;
$R^2$ is H or $C_{1-3}$ alkyl;
$R^3$ is H, $C_{1-10}$ alkyl, heterocycle or aryl; and
R is $C_{1-10}$ alkyl, heterocycle or aryl.

In another aspect, the invention therefore relates to a method of lowering intraocular pressure in a subject in need of such treatment, which comprises administering a therapeutically effective amount of a composition comprising a compound having Formula III, its individual diastereoisomers, its individual hydrates, its individual solvates, its individual crystal forms, its individual isomers, its individual tautomers or a pharmaceutically acceptable salt thereof,

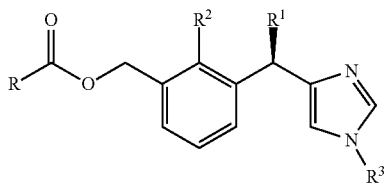

Formula III wherein
$R^1$ is H or $C_{1-3}$ alkyl;
$R^2$ is H or $C_{1-3}$ alkyl;
$R^3$ is H, $C_{1-10}$ alkyl, heterocycle or aryl; and
R is $C_{1-10}$ alkyl, heterocycle or aryl.

The following paragraphs provide definitions of the various chemical moieties that make up the compounds of the invention and are intended to apply uniformly throughout the specification and claims unless expressly stated otherwise.

The term "alkyl" as used herein, is defined as including a saturated monovalent alkane moiety having straight or branched alkane moieties or combinations thereof and containing 1-10 carbon atoms, preferably 1-8 carbon atoms and more preferably 1-4 carbon atoms. Alkyl moieties can optionally be substituted by, but not limited to, amino groups, aryl groups, halogens. One methylene (—$CH_2$—) can be replaced by carbonyl, —NH—, carboxyl, amide, sulfur or by oxygen. Examples include, but are not limited to, methyl, ethyl, propyl, butyl, sec-butyl, pentyl, iso-pentyl, neo-pentyl, hexyl, iso-hexyl, 3-methyl-butyl, 2-amino-N-isobutyl acetamide, iso-butyl, tert-butyl, iso-propyl, ethylphenyl, methylphenyl, 2-amino-3-methyl-butanamide-N-2-methyl-1-propyl, 1-amino-2-methyl-prop-1-yl.

The term "heterocycle" as used herein is defined as an aromatic or non aromatic 5 to 10 membered monocyclic or bicyclic ring containing at least one heteroatom selected from O or N or S or combinations thereof, interrupting the carbocyclic ring structure.

Heterocycles can optionally be substituted by, but not limited to, $C_{1-6}$ alkyl, amino, halogen, —O($C_{1-6}$ alkyl), —OC(O) ($C_{1-6}$ alkyl), —C(O)O($C_{1-6}$ alkyl), —NHC(O)($C_{1-6}$ alkyl), —C(O)NH($C_{1-6}$ alkyl), —S($C_{1-6}$ alkyl) groups. Examples include, but are not limited to, furyl, pyrryl, pyridyl, pyrimidyl, thienyl, isothiazolyl, imidazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,5-thiadiazolyl, 1,2,4-thiadiazolyl, isooxazolyl, quinazolinyl, pyridazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, pyrrolidinyl, piperidinyl and piperazinyl.

The term "aryl" as used herein, is defined as including an organic moiety derived from an aromatic hydrocarbon consisting of a monocyclic or bicyclic ring containing 6-10 carbon atoms by removal of one hydrogen atom, such as phenyl or naphtyl. Aryl groups can optionally be substituted by, but not limited to, $C_{1-6}$ alkyl, amino, halogen, —O($C_{1-6}$ alkyl), —OC(O)($C_{1-6}$ alkyl), —C(O)O($C_{1-6}$ alkyl), —NHC(O)($C_{1-6}$ alkyl), —C(O)NH($C_{1-6}$ alkyl), —S($C_{1-6}$ alkyl) groups. Examples include, but are not limited to, phenyl, naphtyl.

The term "H" as used herein refers to a hydrogen atom.
The term "O" as used herein refers to an oxygen atom.
The term "S" as used herein refers to a sulfur atom.
The term "N" as used herein refers to a nitrogen atom.
The term "amino" as used herein refers to a group of formula —$NH_2$.
The term "amide" as used herein refers to a group of formula —C(O)NH— or —NHC(O)—.
The term "halogen", as used herein refers to an atom of chlorine, bromine, iodine or fluorine.
The term "carbonyl" as used herein refers to a group of formula —C=O.
The term "carboxyl", as used herein refers to a group of formula —C(O)O— or —OC(O)—.

Generally $R^1$ is H or $C_{1-3}$ alkyl. Preferred $R^1$ is $C_{1-3}$ alkyl. Most preferred $R^1$ is methyl.

Generally $R^2$ is H or $C_{1-3}$ alkyl. Preferred $R^2$ is $C_{1-3}$ alkyl. Most preferred $R^2$ is methyl.

Generally $R^3$ is H, $C_{1-10}$ alkyl, heterocycle or aryl. Preferred $R^3$ is H, phenyl or $C_{1-10}$ alkyl. Most preferred $R^3$ is H.

Generally R is $C_{1-10}$ alkyl, heterocycle or aryl. Preferred R is methyl, iso-butyl, tert-butyl, iso-propyl, ethylphenyl, phenyl, 2-amino-1-phenylethyl, 2-(2-amino-3-methyl-butyrylamino)-2-methyl-prop-1-yl, 1-amino-2-methyl-prop-1-yl, 2-(2-amino-acetylamino)-2-methyl-prop-1-yl. Most preferred R groups are tert-butyl, iso-propyl.

As used herein, "tautomer" refers to the migration of protons between adjacent single and double bonds. The tautomerization process is reversible. Compounds described herein can undergo any possible tautomerization that is within the physical characteristics of the compound. The following is a tautomerization example that can occur in compounds described herein:

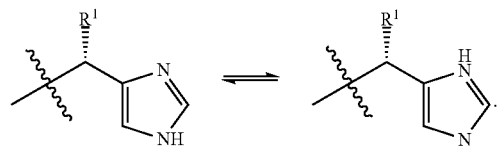

Compounds of the invention are:
iso-Butyric acid 3-[(S)-1-(1H-imidazol-4-yl)ethyl]-2-methyl-benzyl ester;
2,2-Dimethyl-propionic acid 3-[(S)-1-(1H-imidazol-4-yl) ethyl]-2-methyl-benzyl ester;
Acetic acid 3-[(S)-1-(1H-imidazol-4-yl)ethyl]-2-methyl-benzyl ester;
Benzoic acid 3-[(S)-1-(1H-imidazol-4-yl)-ethyl]-2-methyl-benzyl ester;
3-Methyl-butyric acid 3-[(S)-1-(1H-imidazol-4-yl)-ethyl]-2-methyl-benzyl ester;
3-Phenyl-propionic acid 3-[(S)-1-(1H-imidazol-4-yl)-ethyl]-2-methyl-benzyl ester;
2-Amino-3-methyl-butyric acid 3-[(S)-1-(1H-imidazol-4-yl)-ethyl]-2-methyl-benzyl ester;
2-(2-Amino-3-methyl-butyrylamino)-3-methyl-butyric acid 3-[(S)-1-(1H-imidazol-4-yl)-ethyl]-2-methyl-benzyl ester;
2-(2-Amino-acetylamino)-3-methyl-butyric acid 3-[(S)-1-(1H-imidazol-4-yl)-ethyl]-2-methyl-benzyl ester;

2-Amino-3-phenyl-propionic acid 3-[(S)-1-(1H-imidazol-4-yl)ethyl]-2-methyl-benzyl ester.

Intermediates of the invention are:

iso-Butyric acid 3-[(S)-1-(1-iso-butyryl-1H-imidazol-4-yl)-ethyl]-2-methyl-benzyl ester;

2,2-Dimethyl-propionic acid 3-{(S)-1-[1-(2,2-dimethyl-propionyl)-1H-imidazol-4-yl]-ethyl}-2-methyl-benzyl ester;

Acetic acid 3-[(S)-1-(1-acetyl-1H-imidazol-4-yl)-ethyl]-2-methyl-benzyl ester;

Benzoic acid 3-[(S)-1-(1-benzoyl-1H-imidazol-4-yl)-ethyl]-2-methyl-benzyl ester;

3-Methyl-butyric acid 2-methyl-3-{(S)-1-[1-(3-methyl-butyryl)-1H-imidazol-4-yl]-ethyl}-benzyl ester;

Phenyl-propionic acid 2-methyl-3-{(S)-1-[1-(3-phenyl-propionyl)-1H-imidazol-4-yl]-ethyl}-benzyl ester;

2-tert-Butoxycarbonylamino-3-methyl-butyric acid 3-{(S)-1-[1-(2-tert-butoxy carbonylamino-3-methyl-butyryl)-1H-imidazol-4-yl]-ethyl}-2-methyl-benzyl ester;

2-tert-Butoxycarbonylamino-3-methyl-butyric acid 3-[(S)-1-(1H-imidazol-4-yl)-ethyl]-2-methyl-benzyl ester;

2-(2-tert-Butoxycarbonylamino-3-methyl-butyrylamino)-3-methyl-butyric acid 3-{(S)-1-[1-(2-tert-butoxycarbonylamino-3-methyl-butyryl)-1H-imidazol-4-yl]-ethyl}-2-methyl-benzyl ester;

2-(2-tert-Butoxycarbonylamino-3-methyl-butyrylamino)-3-methyl-butyric acid 3-[(S)-1-(1H-imidazol-4-yl)-ethyl]-2-methyl-benzyl ester;

2-(2-tert-Butoxycarbonylamino-acetylamino)-3-methyl-butyric acid 3-[(S)-1-(1H-imidazol-4-yl)ethyl]-2-methyl-benzyl ester;

2-tert-Butoxycarbonylamino-3-phenyl-propionic acid 3-[(S)-1-(1H-imidazol-4-yl)-ethyl]-2-methyl-benzyl ester.

Some compounds of Formula I, Formula II and Formula III and some of their intermediates have at least one stereogenic center in their structure. This stereogenic center may be present in an (R) or (S) configuration, said (R) and (S) notation is used in correspondence with the rules described in Pure Appli. Chem. (1976), 45, 11-13.

Compounds according to the present invention may exist in different polymorphic forms. Although not explicitly indicated in the above formula, such forms are intended to be included within the scope of the present invention.

Compounds of Formula I, Formula II or Formula III and their salts can be in the form of a solvate, which is included within the scope of the present invention. Such solvates include for example hydrates, alcoholates and the like.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I, Formula II or Formula III are able to form.

The acid addition salt form of a compound of Formula I, Formula II or Formula III that occurs in its free form as a base can be obtained by treating the free base with an appropriate acid such as an inorganic acid, for example but not limited to, hydrochloric acid, hydrobromic acid, sulfuric acid, phosphoric acid, nitric acid and the like; or an organic acid such as for example but not limited to, as citric acid, acetic acid, oxalic acid, tartaric acid, succinic acid, malic acid, fumaric acid, ascorbic acid, benzoic acid, tannic acid, palmoic acid, alginic acid, polyglutamic acid, naphthalene-sulfonic acid, napthalenedisulfonic, and polygalacturonic acid as well as base addition salts such as those formed with alkali- and alkaline earth metals such as sodium, potassium and calcium and the like (Handbook of Pharmaceutical Salts, P. Heinrich Stahal& Camille G. Wermuth (Eds), Verlag Helvetica Chemica Acta-Zürich, 2002, 329-345).

The compounds can also be administered as pharmaceutically acceptable quaternary salts known by those skilled in the art, which specifically include, but not limiting to the quaternary ammonium salt of the formula —NY$^+$Z$^-$, wherein Y is hydrogen, alkyl, or benzyl, and Z is a counterion, including but not limited to, chloride, bromide, iodide, —O-alkyl, toluenesulfonate, methylsulfonate, sulfonate, phosphate, or carboxylate (such as fumarate, benzoate, succinate, acetate, glycolate, maleate, malate, fumarate, citrate, tartrate, ascorbate, benzoate, cinnamoate, mandeloate, benzyloate, and diphenylacetate).

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include but are not limited to, glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The present invention concerns also the use of a compound of Formula I, Formula II or Formula III, or a pharmaceutically acceptable salt thereof, for the manufacture of a medicament for the therapeutic application. The present invention concerns also the a method for manufacturing a medicament intended for therapeutic application wherein a compound having general Formula I, Formula II or Formula III, or a pharmaceutically active derivative or salt thereof is used.

Since individual subjects may present a wide variation in severity of symptoms and each drug has its unique therapeutic characteristics, the precise mode of administration and dosage employed for each subject is left to the discretion of the practitioner. The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. The actual amount of the compound to be administered in any given case will be determined by a physician taking into account the relevant circumstances, such as the severity of the condition, the age and weight of the patient, the patient's general physical condition, the cause of the condition, and the route of administration. Additionally, the formulations may be designed to delay release of the active compound over a given period of time, or to carefully control the amount of drug released at a given time during the course of therapy.

Ester pro-drugs of [3-(1-(1H-imidazol-4-yl)ethyl)-2-methylphenyl]methanol, of (S) [3-(1-(1H-imidazol-4-yl)ethyl)-2-methylphenyl]methanol or of (R) [3-(1-(1H-imidazol-4-yl)ethyl)-2-methylphenyl]methanol and their pharmaceutically-acceptable salts may be administered through different routes, including but not limited to topical eye drops, direct injection, application at the back of the eye or formulations that may further enhance the long duration of actions such as a slow releasing pellet, suspension, gel, or sustained delivery devices such as any suitable drug delivery system (DDS) known in the art. While topical administration is preferred, this compound may also be used in an intraocular implant as described in U.S. U.S. Pat. No. 7,931,909 which is hereby incorporated by reference. Such biocompatible intraocular implants include ester pro-drugs of [3-(1-(1H-imidazol-4-yl)ethyl)-2-methylphenyl]methanol, of (S) [3-(1-(1H-imidazol-4-yl)ethyl)-2-methylphenyl]methanol or of (R) [3-(1-(1H-imidazol-4-yl)ethyl)-2-methylphenyl]methanol and a polymer associated with ester pro-drugs of [3-(1-(1H-imidazol-4-yl)ethyl)-2-methylphenyl]methanol, of (S) [3-(1-(1H-imidazol-4-yl)ethyl)-2-methylphenyl]methanol or of (R) [3-(1-(1H-imidazol-4-yl)ethyl)-2-methylphenyl]methanol to facilitate release thereof into an eye for an extended period of time.

Ophthalmic formulations of drug products are well known in the art and described in, for example, U.S. Patent Application Publication No. 20050059583; No. 20050277584; U.S. Pat. No. 7,297,679; and No. 20070015691; and U.S. Pat. Nos. 5,474,979 and 6,582,718, the disclosures of all which are incorporated herein by reference. The ester pro-drugs of [3-(1-(1H-imidazol-4-yl)ethyl)-2-methylphenyl]methanol, of (S) [3-(1-(1H-imidazol-4-yl)ethyl)-2-methylphenyl]methanol or of (R) [3-(1-(1H-imidazol-4-yl)ethyl)-2-methylphenyl]methanol may be formulated with efficacy enhancing components as disclosed in U.S. Pat. No. 7,491,383 B2, which is hereby incorporated by reference in its entirety.

With respect to the present invention reference to a compound or compounds, is intended to encompass that compound in each of its possible isomeric forms and mixtures thereof unless the particular isomeric form is referred to specifically.

The present invention also concerns a process for preparing the compounds having general Formula I, Formula II or Formula III. The synthetic scheme set forth below, illustrates how compounds according to the invention can be made. Those skilled in the art will be able to routinely modify and/or adapt the following scheme to synthesize any compounds of the invention covered by Formula I, Formula II or Formula III.

General Scheme for Synthesizing Ester Prodrugs of (S)-[3-(1-(1H-imidazol-4-yl)ethyl)-2-methylphenyl]methanol

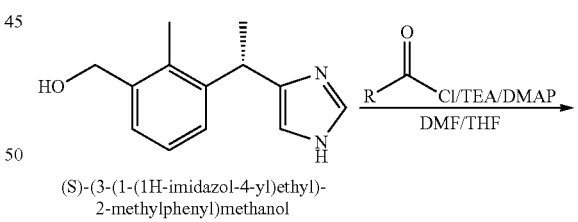

(S)-(3-(1-(1H-imidazol-4-yl)ethyl)-2-methylphenyl)methanol

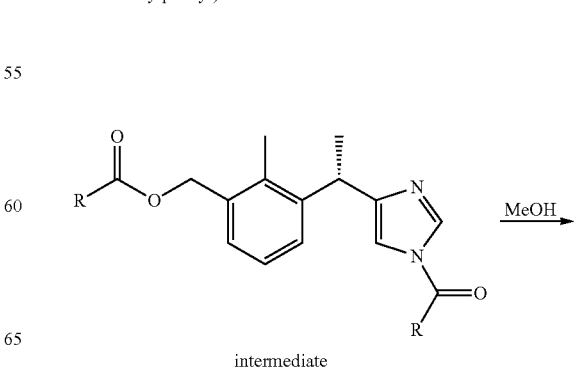

intermediate

-continued

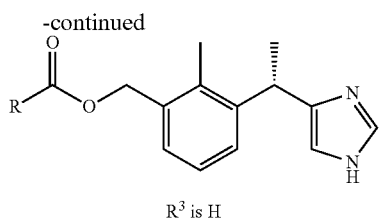

R³ is H

In a first step (S)-[3-(1-(1H-imidazol-4-yl)ethyl)-2-methylphenyl]methanol (CAS 189255-79-6) can react with the desired acyl chloride, in the presence of N,N-dimethyl formamide (DMF), tertahydrofuran (THF), triethylamine (TEA) and 4-dimethyl aminopyridine (DMAP). After a typical work-up by extraction, the residue can be purified by medium pressure liquid chromatography (MPLC) (0% to 40% ethyl acetate in hexanes) to yield the intermediate compound as a solid.

In a second step, the intermediate obtained in the first reaction, can react with methanol (MeOH). The residue can be purified by MPLC (50% ethyl acetate in hexanes then 5% 7N ammonia/methanol/dichloromethane) to yield the desired compound as a solid.

It is to be understood that both the foregoing general description and the following detailed description are exemplary and explanatory only and are not restrictive of the invention claimed. As used herein, the use of the singular includes the plural unless specifically stated otherwise.

The present invention includes all pharmaceutically acceptable isotopically enriched compounds. Any compound of the invention may contain one or more isotopic atoms enriched or different than the natural ratio such as deuterium $^2$H (or D) in place of protium $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

The IUPAC names of the compounds mentioned in the examples were generated with ACD version 8.

Unless specified otherwise in the examples, characterization of the compounds is performed according to the following methods:

NMR spectra are recorded on 300 MHz Varian and acquired at room temperature. Chemical shifts are given in ppm referenced either to internal TMS or to the residual solvent signal.

All the reagents, solvents, catalysts for which the synthesis is not described are purchased from chemical vendors such as Sigma Aldrich, Fluka, Lancaster, however some known reaction intermediates, for which the CAS registry number is mentioned, were prepared in-house following known procedures.

Usually the compounds of the invention were purified by flash column chromatography.

The following abbreviations are used in the examples:
DCM dichloromethane
MeOH methanol
CD$_3$OD deuterated methanol
NH$_3$ ammonia
Na$_2$SO$_4$ sodium sulfate
DMF N,N-dimethylformamide
MgSO$_4$ magnesium sulfate
EtOAc ethylacetate
i-PrOH iso-propanol
CDCl$_3$ deuterated chloroform
MPLC medium pressure liquid chromatography
DMF dimethylformamide
TEA triethylamine
THF tertahydrofuran
DMAP 4-dimethylaminopyridine
RT room temperature
Boc-L-Valine N-(tert-Butoxycarbonyl)-L-valine
Boc-Glycine N-(tert-Butoxycarbonyl)glycine
Boc-L-Phenylalanine N-(tert-Butoxycarbonyl)-L-phenylalanine
HCl hydrochloric acid
H$_2$O water
EDCl 1-ethyl-3-(3-dimethylaminopropyl)carbodiimide
NaHCO$_3$ sodium bicarbonate

EXAMPLE 1

Intermediate 1 iso-Butyric acid 3-[(S)-1-(1-isobutyryl-1H-imidazol-4-yl)-ethyl]-2-methyl-benzyl ester To a solution of (S)-[3-(1-(1H-imidazol-4-yl)ethyl)-2-methylphenyl]methanol (1.34 g, 6.2 mmol) in DMF (8 ml) and THF (50 ml), were added TEA (3.5 ml, 24.8 mmol), DMAP (780 mg, 6.2 mmol) and iso-butyryl chloride (2.18 g, 20.5 mmol). The resulting mixture was stirred at RT for 16 h, quenched with H$_2$O and extracted with ethyl acetate. The combined organic layers were washed with brine, and dried over Na$_2$SO$_4$, and concentrated under reduced pressure. The residue was purified by MPLC (0% to 40% ethyl acetate in hexanes) to yield Intermediate 1 as solid.

$^1$H-NMR (CD$_3$OD, δ ppm): 1.15 (d, J=7.03 Hz, 6H), 1.26 (d, 6H, J=6.74 Hz), 1.56 (d, J=7.03 Hz, 3H), 2.34 (s, 3H), 2.58 (hept, J=7.03 Hz, 1H), 3.34 (hept, J=7.74 Hz, 1H), 4.42 (q, J=7.03 Hz, 1H), 5.15 (s, 2H), 7.07-7.10 (m, 2H), 7.12-7.15 (m, 1H), 7.31 (s, 1H), 8.35 (s, 1H).

Intermediates 2-6 were prepared in a similar manner to the method described in Example 1 starting with (S)-[3-(1-(1H-imidazol-4-yl)ethyl)-2-methylphenyl]methanol. The acyl chloride used in each case and the results are tabulated below in Table 1.

TABLE 1

| Intermediate number | IUPAC name | Acyl chloride | $^1$ NMR (Solvent; δ ppm) |
|---|---|---|---|
| 2 | 2,2-Dimethyl-propionic acid 3-{(S)-1-[1-(2,2-dimethyl- | Pivaloyl chloride | (CD$_3$OD): 1.19 (s, 9H), 1.42 (s, 9H), 1.56 (d, |

TABLE 1-continued

| Intermediate number | IUPAC name | Acyl chloride | $^1$ NMR (Solvent; δ ppm) |
|---|---|---|---|
| | propionyl)-1H-imidazol-4-yl]-ethyl}-2-methyl-benzyl ester | | J = 7.03 Hz, 3H), 2.34 (s, 3H), 4.42(q, J = 7.03 Hz, 1H), 5.15(s, 2H), 7.07-7.10 (m, 2H), 7.12-7.15 (m, 1H), 7.33 (s, 1H), 8.40 (s, 1H). |
| 3 | Acetic acid 3-[(S)-1-(1-acetyl-1H-imidazol-4-yl)-ethyl]-2-methyl-benzyl ester | Acetyl chloride | (CD$_3$OD): 1.55 (d, J = 7.03 Hz, 3H), 2.05 (s, 3H), 2.33 (s, 3H), 2.58 (s, 3H), 4.39(q, J = 7.03 Hz, 1H), 5.15(s, 2H), 7.07-7.10 (m, 2H), 7.12-7.15 (m, 1H), 7.30 (s, 1H), 8.29 (s, 1H). |
| 4 | Benzoic acid 3-[(S)-1-(1-benzoyl-1H-imidazol-4-yl)-ethyl]-2-methyl-benzyl ester: | Benzoyl chloride | (CD$_3$OD): 1.58 (d, J = 7.03 Hz, 3H), 2.43 (s, 3H), 4.46(q, J = 7.03 Hz, 1H), 5.41 (s, 2H), 7.11-7.18 (m, 2H), 7.27-7.35 (m, 2H), 7.42-7.50 (m, 2H), 7.50-7.63 (m, 3H), 7.65-7.71 (m, 1H), 7.79 (d, J = 7.33 Hz, 2H), 8.00 (d, J = 7.33 Hz, 2H), 8/09 (s, 1H). |
| 5 | 3-Methyl-butyric acid 2-methyl-3-{(S)-1-[1-(3-methyl-butyryl)-1H-imidazol-4-yl]ethyl}-benzyl ester | Methylbutanoyl chloride | (CD$_3$OD): 0.91 (d, J = 6.44 Hz, 6H), 1.01 (d, J = 6.44 Hz, 6H), 1.54 (d, J = 7.03 Hz, 3H), 2.05 (hept, J = 6.44 Hz, 1H), 2.15-2.25 (m, 3H), 2.33 (s, 3H), 2.81 (d, J = 7.03 Hz, 3H), 4.42(q, J = 7.03 Hz, 1H), 5.14(s, 2H), 7.07-7.19 (m, 3H), 7.28 (s, 1H), 8.32 (s, 1H). |
| 6 | 3-Phenyl-propionic acid 2-methyl-3-{(S)-1-{1-(3-phenyl-propionyl)-1H-imidazol-4-yl]ethyl}-benzyl ester | Phenylpropanoyl chloride | (CD$_3$OD): 1.52 (d, J = 7.03 Hz, 3H), 2.24 (s, 3H), 2.64 (t, J = 7.61 Hz, 2H), 2.90 (t, J = 7.61 Hz, 2H), 3.04 (t, J = 7.61 Hz, 2H), 3.24 (t, J = 7.61 Hz, 2H), 4.34 (q, J = 7.03 Hz, 1H), 5.13 (s, 2H), 7.08-7.248 (m, 14H), 8.25 (s, 1H). |

EXAMPLE 2

Compound 1 iso-Butyric acid 3-[(S)-1-(1H-imidazol-4-yl)-ethyl]-2-methyl-benzyl ester

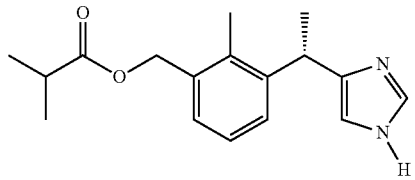 [SMILES: Cc1c(COC(=O)C(C)C)cccc1[C@H](C)c1c[nH]cn1]

Intermediate 1 was dissolved in MeOH (50 ml) and the mixture was stirred at RT for 24 h and then concentrated under reduced pressure. The residue was purified by MPLC (50% ethyl acetate in hexanes then 5% 7N $NH_3$/MeOH/DCM) to yield Compound 1 as a solid.

$^1$H-NMR (CD$_3$OD; δ ppm): 1.15 (d, J=7.03 Hz, 6H), 1.54 (d, J=7.03 Hz, 3H), 2.33 (s, 3H), 2.56 (hept, J=7.03 Hz, 1H), 4.42 (q, J=7.03 Hz, 1H), 5.15 (s, 2H), 6.70 (s, 1H), 7.07-7.10 (m, 2H), 7.12-7.15 (m, 1H), 7.55 (s, 1H).

Compounds 2-6 and of the invention were prepared according to the procedure described in Example 2, by reacting the corresponding intermediate with methanol. The results are tabulated below in Table 2.

TABLE 2

| Comp. No. | IUPAC name | Inter. No. | $^1$NMR (Solvent, δ ppm) |
|---|---|---|---|
| 2 | 2,2-Dimethyl-propionic acid 3-[(S)-1-(1H-imidazol-4-yl)-ethyl]-2-methyl-benzyl ester | 2 | (CD$_3$OD): 1.19 (s, 9H), 1.54 (d, J = 7.03 Hz, 3H), 2.33 (s, 3H), 4.42 (q, J = 7.03 Hz, 1H), 5.13 (s, 2H), 6.70 (s, 1H), 7.07-7.10 (m, 2H), 7.12-7.15 (m, 1H), 7.55 (s, 1H). |
| 3 | Acetic acid 3-[(S)-1-(1H-imidazol-4-yl)-ethyl]-2-methyl-benzyl Ester | 3 | (CD$_3$OD): 1.54 (d, J = 7.03 Hz, 3H), 2.04 (s, 3H), 2.33 (s, 3H), 4.42 (q, J = 7.03 Hz, 1H), 5.13 (s, 2H), 6.70 (s, 1H), 7.07-7.10 (m, 2H), 7.12-7.15 (m, 1H), 7.55 (s, 1H). |
| 4 | Benzoic acid 3-[(S)-1-(1H-imidazol-4-yl)-ethyl]-2-methyl-benzyl ester | 4 | (CD$_3$OD): 1.54 (d, J = 7.03 Hz, 3H), 2.31 (s, 3H), 4.42 (q, J = 7.03 Hz, 1H), 5.13 (s, 2H), 6.70 (s, 1H), 7.07-7.15 (m, 2H), 7.25-7.28 (m, 1H), 7.54-7.47 (m, 2H), 7.55-7.60 (m, 2H), 8.0 (d, J = 7.33 Hz, 2H). |
| 5 | 3-Methyl-butyric acid 3-[(S)-1-(1H-imidazol-4-yl)-ethyl]-2-methyl-benzyl Ester | 5 | (CD$_3$OD): 0.93 (d, J = 7.03 Hz, 6H), 1.54 (d, J = 7.03 Hz, 3H), 2.07 (hept, J = 7.03 Hz, 1H), 2.21 (d, J = 7.03 Hz, 2H), 2.33 (s, 3H), 4.42 (q, J = 7.03 Hz, 1H), 5.15 (s, 2H), 6.70 (s, 1H), 7.07-7.10 (m, 2H), 7.12-7.15 (m, 1H), 7.55 (s, 1H). |

TABLE 2-continued

| Comp. No. | IUPAC name | Inter. No. | ¹NMR (Solvent, δ ppm) |
|---|---|---|---|
| 6 | 3-Phenyl-propionic acid 3-[(S)-1-(1H-imidazol-4-yl)-ethyl]-2-methyl-benzyl Ester | 6 | (CD₃OD): 1.54 (d, J = 7.03 Hz, 3H), 2.23 (s, 3H), 2.65 (t, J = 7.61 Hz, 2H), 2.91 (t, J = 7.61 Hz, 2H), 4.40 (q, J = 7.03 Hz, 1H), 5.13 (s, 2H), 6.70 (s, 1H), 7.08-7.24 (m, 8H), 7.55 (s, 1H). |

EXAMPLE 3

Intermediate 7

2-tert-Butoxycarbonylamino-3-methyl-butyric acid 3-{(S)-1-[1-(2-tert-butoxy carbonylamino-3-methyl-butyryl)-1H-imidazol-4-yl]-ethyl}-2-methyl-benzyl ester To a solution of (S)-[3-(1-(1H-imidazol-4-yl)ethyl)-2-methylphenyl]methanol (216 mg, 1.0 mmol) in DMF (2 ml) and THF (12 ml) were added EDCl (671 mg, 3.5 mmol), DMAP (427 mg, 3.5 mmol) and Boc-L-Valine (651 mg, 3.0 mmol). The mixture was stirred at RT for 16 h, quenched with H₂O and extracted with ethyl acetate. The combined organic layers were washed with H₂O, brine, and dried over Na₂SO₄, and concentrated under reduced pressure. The residue was purified by a column chromatography (30% ethyl acetate in hexanes) to yield Intermediate 7 as a white solid.

¹H-NMR (CD₃OD; δ ppm): 0.85-1.01 (m, 12H), 1.20-1.48 (m, 18H), 1.56 (d, J=7.03 Hz, 3H), 2.01-2.20 (m, 2H), 2.35 (s, 3H), 4.03 (m, 1H), 4.42 (q, J=7.03 Hz, 1H), 4.60-4.65 (m, 1H), 5.15-5.29 (m, 2H), 7.10-7.20 (m, 2H), 7.20-7.25 (m, 1H), 7.33 (s, 1H), 8.44 (s, 1H).

EXAMPLE 4

Intermediate 8

2-tert-Butoxycarbonylamino-3-methyl-butyric acid 3-[(S)-1-(1H-imidazol-4-yl)-ethyl]-2-methyl-benzyl ester The title compound was prepared from Intermediate 7 (600 mg, 0.98 mmol) in 30 ml of MeOH according to the procedure described in Example 2.

¹H-NMR (CD₃OD; δ ppm): 0.85-0.95 (m, 6H), 1.42 (m, 9H), 1.54 (d, J=7.03 Hz, 3H), 2.05 (m, 1H), 2.33 (s, 3H), 4.00 (d, J=6.15 Hz, 1H), 4.40 (q, J=7.03 Hz, 1H), 5.15-5.28 (m, 2H), 6.67 (s, 1H), 7.10-7.20 (m, 2H), 7.20-7.25 (m, 1H), 7.55 (s, 1H).

EXAMPLE 5

Compound 7

2-Amino-3-methyl-butyric acid 3-[(S)-1-(1H-imidazol-4-yl)-ethyl]-2-methyl-benzyl ester

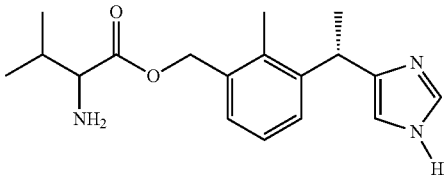 [SMILES: Cc1c(COC(=O)C(N)C(C)C)cccc1[C@H](C)c1c[nH]cn1]

To Intermediate 8 (390 mg, 0.94 mmol) was added 4N HCl in dioxane (8 ml). The resulting solution was stirred at RT for 4 hrs, then quenched with H₂O, neutralized with aqueous saturated NaHCO₃ and extracted with 25% isopropyl alcohol in chloroform. The combined organic layers were dried over Na₂SO₄, and concentrated under reduced pressure. The residue was purified by a column chromatography (5% 7N NH₃/MeOH in DCM) to yield Compound 7 as a white solid.

¹H-NMR (CD₃OD; δ ppm): 0.85 (d, J=6.74 Hz, 3H), 0.91 (d, J=6.74 Hz, 3H), 1.54 (d, J=7.03 Hz, 3H), 1.96 (hept, J=6.74 Hz, 1H), 2.33 (s, 3H), 3.28 (d, J=6.74 Hz, 2H), 4.42 (q, J=7.03 Hz, 1H), 5.20-5.25 (m, 2H), 6.67 (s, 1H), 7.10-7.12 (m, 2H), 7.13-7.20 (m, 1H), 7.55 (s, 1H).

EXAMPLE 6

Intermediate 9

2-(2-tert-Butoxycarbonylamino-3-methyl-butyrylamino)-3-methyl-butyric acid 3-{(S)-1-[1-(2-tert-butoxycarbonylamino-3-methyl-butyryl)-1H-imidazol-4-yl]-ethyl}-2-methyl-benzyl ester The title compound was prepared from Compound 7 (490 mg, 1.55 mmol), Boc-L-Valine (1.01 g, 4.67 mmol), EDCl (1.04 g, 5.42 mmol) and DMAP (671 mg, 5.5 mmol) according to the procedure described in Example 3.

¹H-NMR (CD₃OD; δ ppm): 0.85-0.92 (m, 12H), 1.43 (s, 9H), 1.55 (d, J=7.03 Hz, 3H), 1.97 (m, 1H), 2.14 (hept, J=6.60

Hz, 1H), 2.35 (s, 3H), 3.88 (d, J=7.30 Hz, 1H), 4.35 (d, J=6.90 Hz, 1H), 4.42 (, d, J=7.03 Hz, 1H), 5.18-5.25 (m, 2H), 6.67 (s, 1H), 7.10-7.15 (m, 2H), 7/17-7.20 (m, 1H), 7.55 (s, 1H).

EXAMPLE 7

Intermediate 10

2-(2-tert-Butoxycarbonylamino-3-methyl-butyrylamino)-3-methyl-butyric acid 3-[(S)-1-(1H-imidazol-4-yl)-ethyl]-2-methyl-benzyl ester The title compound was prepared from Intermediate 9 (750 mg, 1.05 mmol) in 30 ml of MeOH according to the procedure described in Example 2.

$^1$H-NMR (CD$_3$OD; δ ppm): 0.89 (d,d, J=7.03 Hz, 6H), 1.44 (s, 9H), 1.54 (d, J=7.33 Hz, 3H), 2.14 (hept, J=6.74 Hz, 1H), 2.33 (s, 3H), 3.74 (s, 2H), 4.35-4.55 (m, 2H), 5.20 (s, 2H), 6.67 (s, 1H), 7.10-7.17 (m, 2H), 7.19-7.23 (m, 1H), 7.56 (s, 1H).

EXAMPLE 8

Compound 8

2-(2-Amino-3-methyl-butyrylamino)-3-methyl-butyric acid 3-[(S)-1-(1H-imidazol-4-yl)-ethyl]-2-methyl-benzyl ester

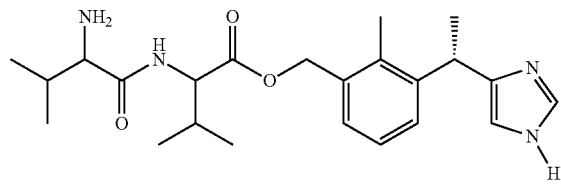 [SMILES: Cc1c(COC(=O)C(NC(=O)C(N)C(C)C)C(C)C)cccc1[C@H](C)c1c[nH]cn1]

The title compound was prepared from Intermediate 10 (450 mg, 0.87 mmol) in 8 ml of 4N HCl/Dioxane according to the procedure described in Example 5.

$^1$H-NMR (CD$_3$OD; δ ppm): 0.85 (d, J=7.03 Hz, 3H), 0.91 (d, J=6.74 Hz, 3H), 0.92 (d, J=7.3 Hz. 3H), 1.14 (d, J=6.2 Hz, 3H), 1.54 (d, J=7.03 Hz, 3H), 1.94 (hept, J=5.2 Hz, 1H), 2.14 (hept, J=6.2 Hz, 1H), 2.33 (s, 3H), 3.18 (d, J=5.2 Hz, 1H), 4.34 (d, J=6.2 Hz, 1H), 4.42 (q, J=7.03 Hz, 1H), 5.21-5.26 (m, 2H), 6.67 (s, 1H), 7.10-7.15 (m, 2H), 7.18-7.20 (m, 1H), 7.55 (s, 1H).

EXAMPLE 9

Intermediate 11

2-(2-tert-Butoxycarbonylamino-acetylamino)-3-methyl-butyric acid 3-[(S)-1-(1H-imidazol-4-yl)-ethyl]-2-methyl-benzyl ester The title compound was prepared from Compound 8 (405 mg, 1.28 mmol), Boc-Glycine (675 mg, 3.86 mmol), EDCl (859 mg, 4.48 mmol) and DMAP (547 mg, 4.48 mmol) according to the procedure described in Example 3. The title compound was purified by column chromatography using 5% 7N NH$_3$/MeOH in DCM.

$^1$H-NMR (CD$_3$OD; δ ppm): 0.89 (d, J=6.74 Hz, 3H), 0.91 (d, J=6.74 Hz, 3H), 1.55 (d, J=7.30 Hz, 3H), 2.14 (hept, J=6.74 Hz, 1H), 2.33 (s, 3H), 4.37 (d, J=5.90 Hz, 1H), 4.42 (q, J=7.03 Hz, 1H), 5.20-5.25 (m, 2H), 6.67 (s, 1H), 7.10-7.12 (m, 2H), 7.13-7.20 (m, 1H), 7.55 (s, 1H).

EXAMPLE 10

Compound 9

2-(2-Amino-acetylamino)-3-methyl-butyric acid 3-[(S)-1-(1H-imidazol-4-yl)-ethyl]-2-methyl-benzyl ester The title compound was prepared from Intermediate 11 (320 mg, 0.68 mmol) with 10 ml of 4N HCl/Dioxane according the procedure described in Example 5.

$^1$H-NMR (CD$_3$OD; δ ppm): 0.89 (d, J=6.74 Hz, 3H), 0.91 (d, J=6.74 Hz, 3H), 2.14 (hept, J=6.74 Hz, 1H), 2.33 (s, 3H), 4.37 (d, J=5.90 Hz, 1H), 4.42 (q, J=7.03 Hz, 1H), 5.20-5.25 (m, 2H), 6.67 (s, 1H), 7.10-7.12 (m, 2H), 7.13-7.20 (m, 1H), 7.55 (s, 1H).

EXAMPLE 11

Intermediate 12

2-tert-Butoxycarbonylamino-3-phenyl-propionic acid 3-[(S)-1-(1H-imidazol-4-yl)-ethyl]-2-methyl-benzyl ester The title compound was prepared from (S)-[3-(1-(1H-imidazol-4-yl)ethyl)-2-methylphenyl]methanol (216 mg, 1.0 mmol), Boc-L-Phenylalanine (795 mg, 3.0 mmol), EDCl (671 mg, 3.5 mmol) and DMAP (427 mg, 3.5 mmol) according to the procedure described in Example 3. Intermediate 12 was purified by a column chromatography using 35-100% ethyl acetate in hexane.

$^1$H-NMR (CD$_3$OD; δ ppm): 1.36 (s, 9H), 1.55 (d, J=7.03 Hz, 3H), 2.28 (s, 3H), 2.85-2.95 (m, 1H), 3.05-3.11 (m, 1H), 4.38 (m, 1H), 4.40 (q, J=7.03 Hz, 1H), 5.17 (s, 2H), 6.69 (s, 1H), 7.08-7.24 (m, 8H), 7.55 (s, 1H).

EXAMPLE 12

Compound 10

2-Amino-3-phenyl-propionic acid 3-[(S)-1-(1H-imidazol-4-yl)-ethyl]-2-methyl-benzyl ester

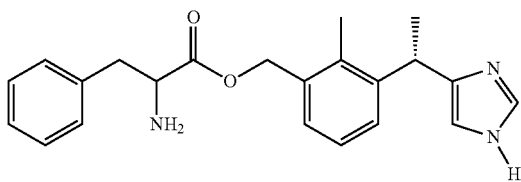 [SMILES: Cc1c(COC(=O)C(N)Cc2ccccc2)cccc1[C@H](C)c1c[nH]cn1]

The title compound was prepared from Intermediate 12 (240 mg, 0.52 mmol) with 8 ml of 4N HCl/Dioxane according to the procedure described in Example 5.

$^1$H-NMR (CD$_3$OD; δ ppm): 1.54 (d, J=7.03 Hz, 3H), 2.26 (s, 3H), 2.90-3.00 (m, 2H), 3.73 (t, J=6.40 Hz, 1H), 4.40 (q, J=7.03 Hz, 1H), 5.13-5.18 (m, 2H), 6.68 (s, 1H), 7.08-7.12 (m, 5H), 7.13-7.22 (m, 3H), 7.55 (s, 1H).

The following assay was used to demonstrate the potency and selectivity of the compounds according to the invention.

EXAMPLE 13

Visual Enhancement Model

Sixteen pigmented (Dutch-Belted) rabbits weighing 2-3 kg are used to evaluate the neuroenhancement effect of pro-drug iso-Butyric acid 3-[(S)-1-(1H-imidazol-4-yl)-ethyl]-2-methyl-benzyl ester. Rabbits are dosed with pro-drug iso-Butyric acid 3-[(S)-1-(1H-imidazol-4-yl)-ethyl]-2-methyl-benzyl ester through intravenous route. Spatial sweep visual evoked potential (sVEP) acuity is assessed with PowerDiva software version 1.8. Recordings were made bilaterally in conscious animals. The results demostrate that pro-drug iso-Butyric acid 3-[(S)-1-(1H-imidazol-4-yl)-ethyl]-2-methyl-benzyl ester enhances visual acuity at 10-30 minutes post-dose in normal DB rabbits.

EXAMPLE 14

The Nerve Crush Model

This example describes the neuroprotective effect of pro-drug iso-Butyric acid 3-[(S)-1-(1H-imidazol-4-yl)-ethyl]-2-methyl-benzyl ester level in the rat nerve crush model. Sprague Dawley rats weighing 300-350 g were anesthetized with a mixture of ketamine (50 mg/kg) and xylazine (0.5 mg/kg). Lateral canthotomy was performed in the right eye and an incision was made in the superior conjunctiva adjacent to the rectus muscle. This was followed by a blunt dissection until optic nerve was exposed. A partial compression was applied to the optic nerve for 30 seconds, 2 to 3 mm distal from the globe, using calibrated cross-acting forceps. Care was taken not to interfere with retinal blood supply. Pro-drug iso-Butyric acid 3-[(S)-1-(1H-imidazol-4-yl)-ethyl]-2-methyl-benzyl ester was administered at 0.03, 0.1, 0.3, 1 mg/kg SC two hours before nerve injury, the vehicle PBS was administered SC as a negative control whereas brimonidine 0.1 mg/kg was given by IP injection as a positive control. Control animals receive phosphate-buffered saline (PBS) vehicle. The experiment was terminated 12-15 days later.

EXAMPLE 15

The Chronic Ocular Hypertension Model

Intraocular Pressure (IOP) was elevated in male Witar rats weighing 350-450 g using laser photocoagulation with blue-green argon laser (Coherent, Palo Alto, Calif.). Rats were anesthetized with a mixture of ketamine (15 mg/kg), acepromazine (1.5 mg/kg), and xylazine (0.3 mg/kg). Laser treatment was done in two parts (1-week interval) on limbal and epsiscleral veins. The amount of energy used was 1 W for 0.2 seconds, delivering a total of 150 spots (50-100 μM). Intraocular pressure was measured using tonometer (TONO-PEN: mentor, Norwell, Mass.). Rats were sedated with 3.0 mg/kg IM acepromazine during IOP measurements. Propa-racaine 0.5% was applied topically on the eyes to anesthetize the cornea. Initial IOP measurements were done before laser treatment to determine baseline IOP and subsequent measurements were done once a week.

Pro-drug iso-Butyric acid 3-[(S)-1-(1H-imidazol-4-yl)-ethyl]-2-methyl-benzyl ester is administered constantly using an osmotic pump (Alzet Osmotic Pumps, Duret Corp., Cupertino, Calif.) which was inserted subcutaneously on the back at 0.03, 0.1, 0.3, 1 mg/kg/day SC two hours before the first laser treatment (preventive mode) or following the second laser treatment (therapeutic mode). The vehicle PBS was administered by SC osmotic pump as a negative control whereas brimonidine 0.1 mg/kg was given by IP injection two hours before the first laser treatment as a positive control. Control animals received phosphate-buffered saline (PBS) vehicle. The experiment was terminated 15-25 days later.

EXAMPLE 16

The Blue Light Model

Pro-drug iso-Butyric acid 3-[(S)-1-(1H-imidazol-4-yl)-ethyl]-2-methyl-benzyl ester is evaluated in the blue light model of retinal degeneration in rats. The drugs is administered continuously with subcutaneous infusion pumps at a dose of 1 mg/kg/day starting two days before blue light exposure. Twenty 4-month old male Sprague Dawley rats (body weight 470-550 g) were used in this study. The animals were exposed to room light on a 12 hour light/12 hour dark cycle before the experiment. All animals were dark adapted overnight (16-20 hours) before blue light. Under the intensity of 6100-6500 lux, rats were exposed to blue light for 4 hours. After the blue light, rats were placed in the dark for another 3 days before returning to normal 12 hour light/12 hour dark. Ocular Coherence Tomography (OCT) measurement was performed at 7 days post blue light exposure. The results demonstrate that blue light exposure with just saline treatment leads to dramatic reduction of retinal thickness measured by OCT, particularly in the superior retina. Histology studies have shown that the reduction in retinal thickness is attributable to loss of photoreceptors. Brimonidine treatment did not prevent the change in retinal thickness while treatment with pro-drug iso-Butyric acid 3-[(S)-1-(1H-imidazol-4-yl)-ethyl]-2-methyl-benzyl ester significantly reduced the damage caused by blue light.

What is claimed is:

1. A method of treating glaucoma or ocular hypertension, in a subject in need of such treatment, which comprises administering a therapeutically effective amount of a composition comprising a compound having Formula I, its individual enantiomers, its individual tautomers or a pharmaceutically acceptable salt thereof,

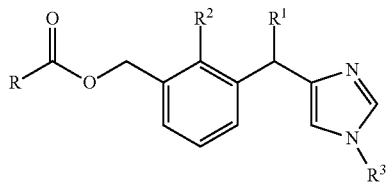

Formula I wherein
R$^1$ is H or C$_{1-3}$ alkyl;
R$^2$ is H or C$_{1-3}$ alkyl;
R$^3$ is H, C$_{1-10}$ alkyl, heterocycle or aryl; and
R is C$_{1-10}$ alkyl, heterocycle or aryl.

2. The method according to claim 1 wherein the compound is of Formula II, its individual tautomers or a pharmaceutically acceptable salt thereof,

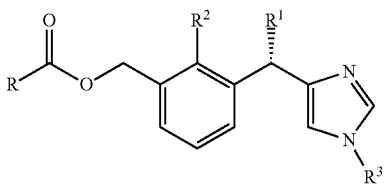

Formula II wherein
R$^1$ is H or C$_{1-3}$ alkyl;
R$^2$ is H or C$_{1-3}$ alkyl;
R$^3$ is H, C$_{1-10}$ alkyl, heterocycle or aryl; and
R is C$_{1-10}$ alkyl, heterocycle or aryl.

3. The method according to claim 1 wherein the compound is of Formula III, its individual tautomers or a pharmaceutically acceptable salt thereof,

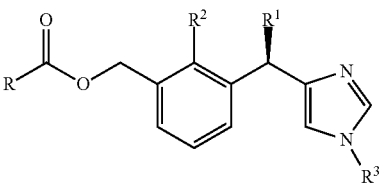

Formula III wherein
R$^1$ is H or C$_{1-3}$ alkyl;
R$^2$ is H or C$_{1-3}$ alkyl;
R$^3$ is H, C$_{1-10}$ alkyl, heterocycle or aryl; and
R is C$_{1-10}$ alkyl, heterocycle or aryl.

4. The method according to claim 2, wherein R$^1$ is C$_{1-3}$ alkyl, R$^2$ is C$_{1-3}$ alkyl R$^3$ is H and R is C$_{1-10}$ alkyl.

5. The method according to claim 2, wherein R$^1$ is methyl, R$^2$ is methyl, R$^3$ is H and R is C$_{1-4}$ alkyl.

6. The method according to claim 2, wherein the compound is selected from:
   iso-Butyric acid 3-[(S)-1-(1H-imidazol-4-yl)ethyl]-2-methyl-benzyl ester;
   2,2-Dimethyl-propionic acid 3-[(S)-1-(1H-imidazol-4-yl) ethyl]-2-methyl-benzyl ester;
   Acetic acid 3-[(S)-1-(1H-imidazol-4-yl)ethyl]-2-methyl-benzyl ester;
   Benzoic acid 3-[(S)-1-(1H-imidazol-4-yl)-ethyl]-2-methyl-benzyl ester;
   3-Methyl-butyric acid 3-[(S)-1-(1H-imidazol-4-yl)-ethyl]-2-methyl-benzyl ester;
   3-Phenyl-propionic acid 3-[(S)-1-(1H-imidazol-4-yl)-ethyl]-2-methyl-benzyl ester;
   2-Amino-3-methyl-butyric acid 3-[(S)-1-(1H-imidazol-4-yl)-ethyl]-2-methyl-benzyl ester;
   2-(2-Amino-3-methyl-butyrylamino)-3-methyl-butyric acid 3-[(S)-1-(1H-imidazol-4-yl)-ethyl]-2-methyl-benzyl ester;
   2-(2-Amino-acetylamino)-3-methyl-butyric acid 3-[(S)-1-(1H-imidazol-4-yl)-ethyl]-2-methyl-benzyl ester; and
   2-Amino-3-phenyl-propionic acid 3-[(S)-1-(1H-imidazol-4-yl)-ethyl]-2-methyl-benzyl ester.

7. The method according to claim 2, wherein the compound is selected from:
   iso-Butyric acid 3-[(S)-1-(1-iso-butyryl-1H-imidazol-4-yl) -ethyl]-2-methyl-benzyl ester;
   2,2-Dimethyl-propionic acid 3-{(S)-1-[1-(2,2-dimethyl-propionyl)-1H-imidazol-4-yl]-ethyl}-2-methyl-benzyl ester;
   Acetic acid 3-[(S)-1-(1-acetyl-1H-imidazol-4-yl)-ethyl]-2-methyl-benzyl ester;
   Benzoic acid 3-[(S)-1-(1-benzoyl-1H-imidazol-4-yl)-ethyl]-2-methyl-benzyl ester;
   3-Methyl-butyric acid 2-methyl-3-{(S)-1-[1-(3-methyl-butyryl)-1H-imidazol-4-yl]-ethyl}-benzyl ester;
   Phenyl-propionic acid 2-methyl-3-{(S)-1-[1-(3-phenyl-propionyl)-1H-imidazol-4-yl]-ethyl}-benzyl ester;
   2-tert-Butoxycarbonylamino-3-methyl-butyric acid 3-{(S)-1-[1-(2-tert-butoxy carbonylamino-3-methyl-butyryl)-1H-imidazol-4-yl]-ethyl}-2-methyl-benzyl ester;
   2-tert-Butoxycarbonylamino-3-methyl-butyric acid 3-[(S)-1-(1H-imidazol-4-yl)-ethyl]-2-methyl-benzyl ester;
   2-(2-tert-Butoxycarbonylamino-3-methyl-butyrylamino)-3-methyl-butyric acid 3-{(S)-1-[1-(2-tert-butoxycarbonylamino-3-methyl-butyryl)-1H-imidazol-4yl]ethyl}-2-methyl-benzyl ester;
   2-(2-tert-Butoxycarbonylamino-3-methyl-butyrylamino)-3-methyl-butyric acid 3-[(S)-1-(1H-imidazol-4-yl)-ethyl]-2-methyl-benzyl ester;
   2-(2-tert-Butoxycarbonylamino-acetylamino)-3-methyl-butyric acid 3-[(S)-1-(1H-imidazol-4-yl)-ethyl]-2-methyl-benzyl ester; and
   2-tert-Butoxycarbonylamino-3-phenyl-propionic acid 3-[(S)-1-(1H-imidazol-4-yl)-ethyl]-2-methyl-benzyl ester.

* * * * *

UNITED STATES PATENT AND TRADEMARK OFFICE
CERTIFICATE OF CORRECTION

PATENT NO. : 8,653,123 B2
APPLICATION NO. : 13/233382
DATED : February 18, 2014
INVENTOR(S) : Mohammad I. Dibas et al.

It is certified that error appears in the above-identified patent and that said Letters Patent is hereby corrected as shown below:

On the title page, item (57), under "Abstract", in column 2, line 5, delete "ethyl) -2" and insert -- ethyl)-2 --, therefor.

In the Specification:

In column 2, lines 34-35, delete "methylphenyl)methanol]" and insert -- methylphenyl]methanol --, therefor.

In column 3, line 19, delete "bowl" and insert -- bowel --, therefor.

In column 3, line 42, delete "rhinophymia" and insert -- rhinophyma --, therefor.

In column 6, line 5, delete "trialklysilyl" and insert -- trialkylsilyl --, therefor.

In column 7, lines 48-62, delete "Heterocycles can optionally be substituted by, but not limited to, $C_{1-6}$ alkyl, amino, halogen, —O($C_{1-6}$ alkyl), —OC(O)($C_{1-6}$ alkyl), —C(O)O($C_{1-6}$ alkyl), —NHC(O)($C_{1-6}$ alkyl), —C(O)NH($C_{1-6}$ alkyl), —S($C_{1-6}$ alkyl) groups. Examples include, but are not limited to, furyl, pyrryl, pyridyl, pyrimidyl, thienyl, isothiazolyl, imidazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,5-thiadiazolyl, 1,2,4-thiadiazolyl, isooxazolyl, quinazolinyl, pyridazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, pyrrolidinyl, piperidinyl and piperazinyl." and insert the same on Col. 7, Line 47, after "carbocyclic ring structure." as a continuation of the same paragraph.

In column 7, line 67, delete "naphtyl." and insert -- naphthyl. --, therefor.

In column 8, line 4, delete "naphtyl." and insert -- naphthyl. --, therefor.

In column 8, line 49, delete "yl)ethyl]" and insert -- yl)-ethyl] --, therefor.

In column 8, lines 51-52, delete "yl)ethyl]" and insert -- yl)-ethyl] --, therefor.

Signed and Sealed this
Seventeenth Day of June, 2014

Michelle K. Lee
*Deputy Director of the United States Patent and Trademark Office*

In column 8, line 53, delete "yl)ethyl]" and insert -- yl)-ethyl] --, therefor.

In column 9, line 2, delete "yl)ethyl]" and insert -- yl)-ethyl] --, therefor.

In column 9, line 17, delete "butoxy carbonylamino" and insert -- butoxycarbonylamino --, therefor.

In column 9, line 29, delete "yl)ethyl]" and insert -- yl)-ethyl] --, therefor.

In column 9, line 64, delete "palmoic acid," and insert -- pamoic acid, --, therefor.

In column 9, lines 65-66, delete "napthalenedisulfonic," and insert -- naphthalenedisulfonic, --, therefor.

In column 10, line 2, delete "Stahal&" and insert -- Stahl & --, therefor.

In column 10, line 3, delete "Chemica" and insert -- Chimica --, therefor.

In column 11, line 29, delete "the a" and insert -- the --, therefor.

In column 13, line 14, delete "tertahydrofuran" and insert -- tetrahydrofuran --, therefor.

In column 14, line 21, delete "tertahydrofuran" and insert -- tetrahydrofuran --, therefor.

In columns 15-16, line 36 (TABLE 1), delete "yl]ethyl}" and insert -- yl]-ethyl} --, therefor.

In columns 15-16, line 48 (TABLE 1), delete "1-{1-" and insert -- 1-[1- --, therefor.

In columns 15-16, line 50 (TABLE 1), delete "yl]ethyl}" and insert -- yl]-ethyl} --, therefor.

In column 19, line 24, delete "butoxy carbonylamino" and insert -- butoxycarbonylamino --, therefor.

In column 23, line 43, delete "demostrate" and insert -- demonstrate --, therefor.

In column 24, line 15, delete "epsiscleral" and insert -- episcleral --, therefor.

In column 24, line 26, delete "Duret" and insert -- Durect --, therefor.

In the Claims:

In column 25, line 67, in claim 4, delete "$C_{1-3}$ alkyl" and insert -- $C_{1-3}$ alkyl, --, therefor.

In column 26, line 5, in claim 6, delete "yl)ethyl]" and insert -- yl)-ethyl] --, therefor.

In column 26, lines 7-8, in claim 6, delete "yl)ethyl]" and insert -- yl)-ethyl] --, therefor.

In column 26, line 9, in claim 6, delete "yl)ethyl]" and insert -- yl)-ethyl] --, therefor.

In column 26, line 29, in claim 7, delete "yl) -ethyl]" and insert -- yl)-ethyl] --, therefor.

In column 26, line 42, in claim 7, delete "butoxy carbonylamino" and insert -- butoxycarbonylamino --, therefor.

In column 26, line 49, in claim 7, delete "-4yl]ethyl}" and insert -- -4-yl]-ethyl} --, therefor.